United States Patent [19]

De Villez

[11] Patent Number: 4,923,900

[45] Date of Patent: May 8, 1990

[54] THERAPEUTIC COMPOSITIONS CONTAINING BENZOYL PEROXIDE

[75] Inventor: Richard L. De Villez, San Antonio, Tex.

[73] Assignee: Board of Regents, The University of Texas System, Austin, Tex.

[21] Appl. No.: 862,808

[22] Filed: May 13, 1986

Related U.S. Application Data

[63] Continuation-in-part of Ser. No. 694,226, Jan. 24, 1985, abandoned.

[51] Int. Cl.$^5$ ............................................. A61K 3/075
[52] U.S. Cl. ................................... 514/714; 514/859; 514/862; 514/864
[58] Field of Search ......................................... 514/714

[56] References Cited

U.S. PATENT DOCUMENTS

| | | | |
|---|---|---|---|
| 3,699,230 | 10/1972 | Beauchanp et al. | 514/376 |
| 3,828,104 | 8/1974 | Barnhurst et al. | 424/45 |
| 4,056,611 | 11/1977 | Young | 424/62 |
| 4,082,881 | 4/1978 | Chen et al. | 514/172 X |
| 4,163,800 | 8/1979 | Wickett et al. | 424/326 |
| 4,189,501 | 2/1980 | Fulton, Jr. | 424/338 |
| 4,350,681 | 9/1982 | Fulton, Jr. | 424/53 |
| 4,355,028 | 10/1982 | Kligman et al. | 424/230 |
| 4,361,584 | 11/1982 | Fulton, Jr. | 424/338 |
| 4,387,107 | 6/1983 | Klein et al. | 424/338 |
| 4,401,835 | 8/1983 | Tarasov | 568/559 |
| 4,411,893 | 10/1983 | Johnson et al. | 424/181 |
| 4,446,145 | 5/1984 | Van Bever | 424/273 |
| 4,451,480 | 5/1984 | DeVillez | 424/278 |

OTHER PUBLICATIONS

Aldrich Chemical Co., 1984–1985 catalog, p. 231.
Section of Separation and Purification, ed. by Weissburger, VII, pp. 475–478.
Section of Modern Experimental Organic Chemistry, Roberts et al., pp. 50–54.

*Primary Examiner*—Leonard Schenkman
*Attorney, Agent, or Firm*—Arnold, White & Durkee

[57] ABSTRACT

A stable composition and method for cutaneous therapy, particularly for treatment of acne, dermatophyte infection, poison ivy reactions and body odor development. The composition includes benzoyl peroxide particles, water and a solvent for benzoyl peroxide which has a boiling point substantially greater than 100° C. Evaporation of the water leaves a solvent-benzoyl peroxide solution particularly non-irritative and effective in activity against cutaneously abiding microorganisms and contactants characteristic of certain plants.

18 Claims, No Drawings

THERAPEUTIC COMPOSITIONS CONTAINING BENZOYL PEROXIDE

This application is a continuation-in-part of pending prior application Ser. No. 06/694,226 filed Jan. 24, 1985 and now abandoned.

BACKGROUND OF THE INVENTION

The present invention relates to topically applicable compositions useful and particularly effective for treatment of dermatological lesions and prevention of other adverse effects of microorganism growth on skin.

Dermatological lesions, including acne, seborrhea, tinea (ringworm) infections, tinea cruris (jock itch), tinea pedis (athletes' foot) and reaction to plant contactants such as the oleoresins of poison ivy, are prevalent medical problems.

Acne and seborrhea are human skin conditions characterized by an excessive flow of sebum (skin oil) from the sebaceous glands located in the pilosebaceous apparatus. Sebum travels through hair follicle ducts to the skin surface. Excessive sebum in or near these ducts may act to block the flow of sebum to the skin surface. Such blocking in turn may produce a thickening and solidification of the sebum to form a solid plug termed a comedone. Comedone formation may stimulate hyperkeratinigation of the hair follicle openings to induce even further blockage or complete closure of the ducts. As a result of this blockage, papules, pustules or cysts may result and are often contaminated with bacteria, whose proliferations cause secondary infections. Acne, and seborrhea to a lesser extent, are particularly characterized by the presence of comedones, inflammatory papules, pustoles or cysts. The suppression or elimination of these secondary bacterial infections will result in a return to sound dermatological health. Many treatments have been tested to achieve the elimination of these secondary dermatological infections and their too frequent results of dermatological and/or psychological scarring. No treatments thus far tested have solved this medical problem in a generally satisfactory manner.

Various fungi, often termed dermatophytes, are able to colonize areas of the skin resulting in irritating, or even disfiguring and infectious dermatological lesions. The suppression and elimination of these dermatophyte infections such as ringworm, athletes foot, and jock itch have also been an object of the medical profession.

Exposure of many individuals to allergenic plants such as poison ivy may result in dermatological lesions such as painful and irritating skin rashes. The prevention and alleviation of such plant-induced rashes is another long-standing object of the medical profession.

Microbes present on the skin, particularly when allowed to proliferate in moist skin areas, are thought to be causes of objectionable body odor. The prevention of such objectionable body odor in those susceptible thereto is a well-established desire of many people.

Benzoyl peroxide, $(C_6H_5CO)_2O_2$ (BZP), is a potent nontoxic oxidant which has long been used for treatment of dermatological lesions and known to be an effective anti-microbial and anti-keratolytic agent useful, for example, in the treatment of acne. Difficulties noted with BZP preparations have included BZP chemical instability. In its particulate solid form BZP has been found to be generally more stable than it's dissolved form. However, when a preparation containing BZP particles is utilized to treat dermatological lesions, the BZP particles eventually contacting the skin may have adverse irritative effects. These adverse effects appear to result, at least in part, from the excessive concentrations of BZP at skin areas in contact with BZP particles. Methods of avoiding such adverse effects while still effectively utilizing BZP therapeutically are long-sought. Therapeutic preparations comprising BZP particles and glycerol have been commonly utilized. Glycerol is generally acknowledged not be be a solvent for BZP, but to be a soothing emollient for skin.

Certain prior attempts to create stable, pharmaceutically effective and dermatologically non-irritative BZP preparations have involved the production of minute BZP crystals. For example, U.S. Pat. No. 4,401,835, issued to Tarasov, describes a method of preparing BZP crystals ranging below ten microns in size. The procedure of U.S. Pat. No. 4,401,835 was described as comprising: (1) preparing a first solution comprising BZP and a "precipitate promoting material." (The "precipitate promoting material" was a solvent for BZP preferably able to produce a solution containing up to about 15% by weight BZP. In the preferred embodiment the "precipitate promoting material" is the dimethyl ether of 1,4:3,6-dianhydrosorbitol (dimethyl isosorbide) or tetrahydrothiophene-1,1-dioxide); (2) adding (preferably slowly with vigorous agitation) the first solution to a second solution wherein the BZP precipitates as a fine crystalline dispersion. (The second solution comprised an aqueous solution of a non-toxic dispersant which was non-reactive with BZP. This dispersant was a cellulose derivative or a surfactant (non-ionic or anionic)); and (3) recovering the five BZP crystals (which may be washed if desired or used directly).

Even very fine BZP crystals are, of course, still finite particles. Such particles may contact the skin and generate high BZP concentrations at such points of contract.

One object of the present invention is to minimize or avoid the contact of BZP particles with the skin of an individual being treated with a BZP preparation.

A further object of the present invention is a BZP preparation which is stable and, after application to the skin of an individual, results in the contact of a BZP solution with the skin areas being treated.

SUMMARY OF THE INVENTION

The present invention comprises a composition for cutaneous therapy. The composition includes benzoyl peroxide particles; water and a solvent. The solvent is water miscible and has a normal boiling point substantially greater than about 100° C. The solvent is also a solvent for benzoyl peroxide.

DETAILED DESCRIPTION OF THE PREFERRED EMBODIMENT

The present invention concerns benzoyl peroxide-containing formulations or compositions for dermal treatment or therapy. Benzoyl (BZP), a solid under the usual ambient conditions, is largely water insoluble. Suspensions of BZP particles have long been used for treatment of cutaneous lesions. However, to the inventor's knowledge, a therapeutic preparation comprising water, a water-miscible solvent for BZP having a normal boiling point substantially above 100° C. and BZP particles has not here before been found.

Advantageous features of the composition of the present invention are thought to hinge, at least in part, upon the unique effects of BZP solubility or insolubility in particular liquids and liquid combinations. These theories of therapeutic effectiveness are presented as elucidating and are not meant to represent limitations of the invention unless otherwise specifically indicated herein.

BZP is generally stable in a solid form such as particles or crystals. BZP particles, however, as discussed earlier, may have irritative dermatological effects. BZP is soluble in solvents comprised by the composition of the present invention. The term soluble as used herein is defined as dissolving at least to a concentration of about 1 gram BZP per 100 ml of solvent. The term insoluble as used herein is defined as having solubility substantially less than 1 gram per 100 ml. These solvents are organic in nature, meaning that they comprise carbon atoms, and they are miscible with water. The term miscible as used herein is defined as being able to form a generally homogeneous solution. BZP is insoluble in water and soluble in the solvents discussed and used herein. As water is mixed with BZP dissolved in a water miscible solvent, the BZP becomes insolubilized and precipitates or crystallizes. This mechanism has been described in U.S. Pat. No. 4,401,835, issued to Tarasov which is incorporated by reference herein.

In one view, the present invention involves the in situ transition of BZP from a solid to a dissolved form. This in situ transition on the skin of a patient being treated represents a unique advantage of the present invention. After dissolution of the BZP, no particles irritate the skin and the dissolved BZP may permeate pathological skin structures. No prior BZP preparations demonstrate such activities. A fluid medium is utilized, this fluid medium being a mixture primarily comprising a solvent, water and BZP particles. The solvent of the present invention has a number of desired characteristics which include the following:

1. BZP is soluble in the solvent such that a solution of at least about 3% BZP by weight forms under ambient conditions of temperature.
2. The solvent is miscible with water such that substantially homogeneous water-solvent solutions may form.
3. BZP becomes substantially less soluble in water-solvent solutions as the water content thereof increases.
4. The solvent does not chemically react with the BZP under ambient conditions of temperature.
5. The solvent evaporates from a water-solvent mixture more slowly than does water from said mixture.
6. The solvent is preferably a liquid at temperatures down to at least about 25° C.
7. The solvent is non-toxic and not dermatologically irritating.

Further preferable characteristics of this solvent include: a lack of objectionable odor; a lack of noticeable color; and, an absence of tendencies to induce comedones (i.e. hypocomedonicity).

In a therapeutic situation, a composition comprising BZP particles, water and a dermatologically acceptable solvent for BZP, said solvent having a normal boiling point substantially greater than about 100° C. and being miscible with water, is prepared and applied to the desired areas of skin to be treated. The term "dermatologically acceptable", as used herein, is defined as suitable for use in contact with tissues of humans and lower animals without undue toxicity, irritation, allergic response and the like, commensurate with a reasonable benefit/risk ratio. The term "normal boiling point" is used herein to mean the temperature of boiling under normal ambient conditions of pressure.

The composition comprising BZP particles, after application to the skin, is subject to body heat and ambient air. The water of the composition proceeds to evaporate at a more rapid rate than the solvent. This evaporation results in a residue comprising solvent and BZP. The BZP particles dissolve in the solvent during and after the evaporation of water, thus precluding or inhibiting skin irritation by particulate BZP. This residue comprises a BZP-solvent solution. The BZP-solvent solution may effectively inhibit the growth of microorganisms such as bacteria or fungi both on the skin surface and within normal skin structures or pathological skin structures such as pustules, for example. Such residual BZP-solvent solutions may also be used in the deactivation of irritative plant contactants such as the oleoresins of poison ivy.

Described by U.S. Pat. No. 4,401,835 and termed therein "precipitate promoting material" are water miscible solvents for BZP which are non-reactive with BZP. Some of these solvents were selected from the group consisting of sulfur-containing aliphatic ethers, long-chain aliphatic and araliphatic ethers, ethylene oxide derivatives, and mixtures thereof Preferable "precipitate-promoting material" in U.S. Pat. No. 4,401,835 was selected from the group consisting of: dimethyl ether of 1,4; 3,6 dianhydrosorbitol, tetrahydrothiophene -1,1-dioxide, dimethyl sulfoxide, ethylene glycol diacetate, Cellosolve ® acetate, (2-ethoxyethyl acetate) propylene carbonate and mixtures thereof In the most preferred embodiments of U.S. Pat. No. 4,401,835, the precipitate promoting material was the dimethyl ether of 1,4; 3,6-dianhydrosorbitol (i.e. dimethylisosorbide) or tetrahydrothiophene-1,1 dioxide.

Many of the "precipitate promoting materials" discussed above, insofar as they are water-miscible, have boiling points greater than 100° C., and are dermatologically acceptable, are usable in the practice of the present invention as described herein. Although the solvents of the present invention are described in terms of boiling points substantially greater than 100° C., this is merely for convenience. A critical characteristic of such solvents is that it evaporates from an aqueous mixture on the skin at a rate much less than that of accompanying water. The dermatological acceptability of usable solvents are readily determined by observation of well-known standard pharmaceutical or dermatological references and/or simple skin sensitivity testing both of these processes being routine to those skilled in the art. The solvents of the present invention may be used alone or in combination.

A particularly preferred solvent of the present invention is dimethylisosorbide (1,4 3,6-dianhydrosorbitol 2,5-dimethyl ether), available from the Aldrich Chemical Co. as isosorbide dimethyl ether. This particularly preferred solvent is established as being dermatologically acceptable.

The water comprised in the compositions of the present invention is preferably between about 30% by weight and about 94% by weight of the composition.

Further ingredients of the composition of the present invention may include pharmaceutically acceptable additives commonly used to facilitate formation of physically or cosmetologically desirable formulations such as salves, creams, foams or lotions. By the term "pharmaceutically acceptable", the qualities of non-toxicity, non-irritativity and relative stability are meant herein. Such additives, for example, may include alkyl alcohols such as cetyl alcohol, for example, to control composition viscosity. Emulsifiers such as Promulgen-G [Amerchol Corp., cetearyl alcohol and ceterareth-20 chemical composition, a blend of cetyl/stearyl alcohol and the ethoxylates of these alcohols] to emulsify the composition and anti-foaming agents such as Simethicone [Dow Corning or Union Carbide USP standard 90.5 to 99.0% polydimethylsiloxane] to prevent foaming may be present in the composition for their various advantageous physical effects in formation of a readily applied cream, salve, foam or lotion.

The composition of the present invention for cutaneous therapy comprises benzoyl peroxide particles. The BZP particles are preferably between about 1% by weight and about 20% by weight of the compositions. Further comprised in the compositions is a water miscible, dermatologically acceptable solvent for benzoyl peroxide, said solvent having a normal boiling point substantially greater than 100° C. This solvent most preferably has a rate of evaporation from the composition substantially less than the rate of water evaporation from the composition when said composition is exposed to air under ambient conditions. The solvent is preferably between about 5% by weight and about 50% by weight of the composition. By the term "cutaneous therapy" is meant any treatment of adverse skin conditions related to the presence of foreign organisms or materials.

The compositions of the present invention may be utilized to effectively alleviate cutaneous conditions such as: acne and seborrhea; dermatophyte infection; reactions to irritative plant contactants such as the oleoresins of poison ivy; and development offensive body odor.

The following examples are presented to further illustrate preferred embodiments of the present invention but are not intended to limit the present invention unless otherwise specifically so indicated herein.

EXAMPLE 1

BZP Composition

A BZP composition was prepared containing the following ingredients:

|  | Percent by Weight |
| --- | --- |
| Cetyl alcohol | 1.0 |
| Promulgen-G | 5.0 |
| 70% benzoyl peroxide (aqueous suspension) | 7.15 |
| Simethicone | 0.10 |
| dimethylisosorbide | 25.0 |
| dionized water | 61.75 |

The above ingredients were mixed to form a homogeneous composition. The 70% benzoyl peroxide suspension was a USP standard hydrous benzoyl peroxide preparation The Promulgen-G and Simethicone were those described above. The cetyl alcohol (hexadecanol) preparation utilized was at least 90% cetyl alcohol, the residual being chiefly stearyl alcohol. Dimethylisosorbide was obtained from the Aldrich Chemical Company, P.O. Box 2060, Milwaukee, Wis. 65321, as number 24,789-8 isosorbide dimethyl ether (98%).

This composition was utilized in subsequently described stability studies and cutaneous therapies.

After departure of water, for example due to evaporation, the residue had the following composition:

|  | Percent by Weight |
| --- | --- |
| Cetyl alcohol | 2.77 |
| Promulgen-G | 13.85 |
| benzoyl peroxide | 13.85 |
| Simethicone | 0.28 |
| dimethylisosorbide | 69.25 |

EXAMPLE 2

Stability of Benzoyl Peroxide

A BZP composition as described in Example 1 was prepared and stored at room temperature in a closed container. Samples were periodically withdrawn and assayed for BZP. The BZP was assayed as directed in the Official Monographs of the United States Pharmacopea XX (pg. 76). Briefly, this assay involved: diluting a portion of the composition in acetone; adding phenyl sulfide; adding potassium iodide and incubating protected from light for 15 min.; adding additional acetone and titrating liberated iodine with 0.01N sodium thiosulfate VS to a colorless end-point. It was found that the benzoyl peroxide content of the composition was essentially unchanged after as much as 22 months of storage.

EXAMPLE 3

Acne

Six young adult patients with grade III pustular-papular acne were contacted. These patients had previously utilized commercially available BZP facial treatments and reported facial skin irritation and poor therapeutic efficacy.

These six patients with grade III pustular-papular acne were treated with the BZP composition described in Example 1. Applications of this composition to the facial skin of the patients were done thrice daily for six weeks and no other treatment was utilized. After the six-week treatment period, all patients exhibited clinically observable improvement. The patients continued to use treatment with the composition for more than a year without significant adverse effects. Two of the patients discontinued use of the composition after about one year and remained dermatologically clear. Two other patients decreased their treatment with the composition to once daily, while the final two patients continued to retain satisfactory dermatological results by a twice daily usage. All six patients reported use of the present BZP preparation without facial irritation. Thus a regular usage of a BZP preparation was made more acceptable in view of decreased irritative side effects found from dermal therapy with the composition of the present invention. This ease of usage is one factor in the increased therapeutic efficacy of the compositions of the present invention. As compared to prior available BZP preparations, it was generally agreed that the BZP preparation of the present invention was both less irritating and more therapeutically effective than any commercially available BZP preparation tested before.

EXAMPLE 4

Dermatophyte Infection

Six patients with dermatophyte infections were treated twice daily in the infected dermal areas for six weeks with the composition described in Example 1. Two patients had tinea corporis (ringworm) infections on the face and neck. One patient had tinea cruris (jock itch) and three patients had tinea pedis (athlete's foot). After the six week period of treatment, all six patients had cleared their infection as confirmed by direct microscopic evaluation of an aqueous potassium hydroxide suspension of cutaneous scrapings and by attempted dermatophyte culture from cutaneous scrapings.

Two patients with tinea versicolor reported who had previously been treated topically with accepted selenium sulfide and imidazole anti-fungal preparations. These prior treatments had not relieved their fungal infections. These two patients were topically treated for six weeks with the BZP composition described in Example 1. The tinea versicolor infections were thereby cured and no recurrences occurred for at least a two year period. The superiority of the BZP preparation of the present invention to prior antifungal treatments was thus demonstrated.

Five young adults were interviewed who had been treating their tinea corporis infections with a variety of available over-the-counter antifungal preparations for 2-3 weeks. These five patients had noted little abatement of their infections with these antifungal preparations. After two weeks of topical treatment with the BZP composition of Example 1, the patients' tinea corporis infections had cleared.

Fungal infections have not been routinely treated with BZP. BZP was known to have fungicidal and/or fungistatic effect, but, due to irritation of the available therapeutic compositions, it had been impractical to use it topically. The therapeutic composition of the present invention is not irritating and therefore may be used to treat cutaneous fungal disease.

EXAMPLE 5

Poison Ivy

Two guinea pigs were sensitized to poison ivy by exposure thereto. Each sensitized guinea pig had five cutaneous areas separately designated. Area 1 had the BZP composition of Example 1 applied one hour before exposure to the poison ivy contactant. Area 2 had the BZP composition applied immediately before exposure to the contactant. Area 3 had an application of the BZP composition immediately after exposure to the contactant. Area 4 had the composition applied about found hours after exposure to the contactant. Area 5 had no treatment with the composition but was exposed to the contactant.

After a one-day period, skin blisters typical of poison ivy exposure developed in areas 4 and 5 but not in areas 1, 2 and 3. The composition was effective in preventing dermal reactions to contactants such as the oleoresin of poison ivy. Composition treatment of skin before exposure to or immediately (less than 4 hours) after exposure to such contactants alleviated development of adverse dermatological reactions.

EXAMPLE 6

Deodorants

Two individuals utilized applications of the composition, particularly in armpit areas and reported that the applications prevented occurrence of objectionable body odor. The development of offensive body odor was thus alleviated.

Changes may be made in composition ingredients and the procedures of use or their sequence as described herein without departing from the spirit and scope of the present invention as described in the following claims.

What is claimed is:

1. A method for alleviation of an individual's acne, seborrhea, dermatophyte infection, reaction to irritative plant contactants or body order, the method including
    applying to affected skin areas of the individual a therapeutically effective amount of a composition comprising:
        benzoyl peroxide particles in a quantity between about 1% by weight and about 20% by weight of the composition;
        water in a quantity between about 30% by weight and about 94% by weight of the composition; and
        demethylisosorbide in a quantity between about 5% by weight and about 50% by weight of the composition.

2. The method of claim 1 wherein the composition is defined further as comprising:
    about 7.15% by weight benzoyl peroxide;
    about 61.75% by weight water; and
    about 25% by weight dimethylisisorbide.

3. The method of claim 1 wherein the benzoyl peroxide particles are defined further as being crystals.

4. The method of claim 1 wherein the composition is defined further as comprising an alkyl alcohol in a quantity sufficient to control the viscosity of the composition.

5. The method of claim 1 wherein the composition is defined further as comprising cetyl alcohol in a quantity sufficient to control the viscosity of the composition.

6. The method of claim 1 wherein the composition is defined further as comprising a blend of cetyl/stearyl alcohol and ethoxylates thereof, in a quantity sufficient to control the viscosity of the composition.

7. The method of claim 1 wherein the composition is defined further as comprising an anti-foaming agent in a quantity sufficient to prevent foaming.

8. The method of claim 1 wherein the composition is defined further as comprising polydimethylsiloxane in a quantity sufficient to prevent foaming.

9. The method of claim 1 wherein the composition is defined further as including pharmaceutically acceptable additives to enhance formation of a cream, salve, foam or lotion.

10. A method for prevention of cutaneous reaction to irritative plant contactants, the method including
    applying to a cutaneous area exposed to the plant contactants a therapeutically effective amount of a composition comprising:
        benzoyl peroxide particles in a quantity between about 1% by weight and about 20% by weight of the composition;

water in a quantity between about 30% by weight and about 94% by weight of the composition; and dimethylisosorbide in a quantity between about 5% by weight and about 50% by weight.

11. The method of claim 10 wherein the composition is defined further as comprising an alkyl alcohol.

12. The method of claim 10 wherein the composition is defined further as comprising cetyl alcohol.

13. The method of claim 10 wherein the composition is defined further as comprising an emulsifier in a quantity sufficient to emulsify the composition.

14. The method of claim 10 wherein the composition is defined further as including pharmaceutically acceptable additives to enhance formation of a cream, salve, foam or lotion.

15. The method of claim 10 wherein the benzoyl peroxide particles are defined further as being crystals.

16. The method of claim 10 wherein the composition is defined further as comprising a blend of cetyl/stearyl alcohol and the ethoxylates thereof to control viscosity of the composition.

17. The method of claim 10 wherein the composition is defined further as comprising an anti-foaming agent.

18. The method of claim 10 wherein the composition is defined further as comprising polydimethylsiloxane.

* * * * *

UNITED STATES PATENT AND TRADEMARK OFFICE
CERTIFICATE OF CORRECTION

PATENT NO. : 4,923,900

DATED : May 8, 1990

INVENTOR(S) : Richard L. De Villez

It is certified that error appears in the above-identified patent and that said Letters Patent is hereby corrected as shown below:

In claim 1, column 8, line 28 delete the term "demethylisosorbide" and insert the term --dimethylisosorbide--.

In claim 2, column 8, line 36 delete the term "dimethylisosorbide--.

Signed and Sealed this

Fourteenth Day of January, 1992

Attest:

HARRY F. MANBECK, JR.

*Attesting Officer*         *Commissioner of Patents and Trademarks*